US006759056B2

(12) United States Patent
Jordan

(10) Patent No.: US 6,759,056 B2
(45) Date of Patent: Jul. 6, 2004

(54) MIXTURE FOR TRANSDERMAL DELIVERY OF LOW AND HIGH MOLECULAR WEIGHT COMPOUNDS

(75) Inventor: Frederick L. Jordan, Santa Ana, CA (US)

(73) Assignee: Oryxe, Irvine, CA (US)

( * ) Notice: Subject to any disclaimer, the term of this patent is extended or adjusted under 35 U.S.C. 154(b) by 94 days.

(21) Appl. No.: 10/183,764

(22) Filed: Jun. 25, 2002

(65) Prior Publication Data

US 2003/0064093 A1 Apr. 3, 2003

Related U.S. Application Data

(63) Continuation of application No. 09/350,043, filed on Jul. 8, 1999.
(60) Provisional application No. 60/092,061, filed on Jul. 8, 1998.

(51) Int. Cl.$^7$ .............................. A61K 9/70; A61K 9/14
(52) U.S. Cl. ....................... 424/449; 424/484; 514/937; 514/938
(58) Field of Search ................................ 424/449, 484; 514/937, 938

(56) References Cited

U.S. PATENT DOCUMENTS

| | | | |
|---|---|---|---|
| 5,318,960 A | 6/1994 | Toppo | 514/159 |
| 5,431,924 A | 7/1995 | Ghosh et al. | |
| 5,472,713 A | 12/1995 | Fein et al. | |
| 5,571,671 A | 11/1996 | Potter | 435/6 |
| 5,614,212 A | 3/1997 | D'angelo et al. | 424/449 |
| 5,665,378 A | 9/1997 | Davis et al. | 424/448 |
| 5,708,038 A | 1/1998 | Davis | 514/783 |
| 5,716,625 A | 2/1998 | Hahn et al. | |
| 5,744,368 A | 4/1998 | Goldgaber et al. | 436/501 |
| 5,837,853 A | 11/1998 | Takashima et al. | 536/24.5 |
| 5,840,746 A | 11/1998 | Ducharme et al. | 514/438 |
| 5,849,334 A | 12/1998 | Rivlin | |
| 5,861,268 A | 1/1999 | Tang et al. | 435/25 |
| 5,885,597 A | 3/1999 | Botknecht et al. | 424/401 |
| 5,891,651 A | 4/1999 | Roche et al. | 435/21 |
| 5,891,857 A | 4/1999 | Holt et al. | 514/44 |
| 5,958,384 A | 9/1999 | Holick | |
| 6,103,246 A | 8/2000 | Tisdale et al. | |

FOREIGN PATENT DOCUMENTS

| | | |
|---|---|---|
| WO | WO 92/08470 | 5/1992 |
| WO | WO 97/09992 A1 | 3/1997 |
| WO | WO 98/03163 | 1/1998 |
| WO | WO 98/33474 | 8/1998 |
| WO | WO 98/34629 | 8/1998 |

OTHER PUBLICATIONS

O'Malley, P. et al., "Emu Products, Increasing Production and Profitability," *Rural Industries & Development Corporation*, pp. i–110, Dec. 1999.

Downing et al., *Dermatology in General Medicine*, Fitzpatrick, et al., eds., pp. 210–221 (1993).
Ponec, M., *Epidermal lipids in vivo, The Keratinocyte Handbook*, Leigh, et al., eds., pp. 351–363 (1994)).
Woodin, L., *Cutting postop pain, RN*, Aug.: 26–33 (1993).
Amadio et al., *Nonsteroidal anti–inflammatory drugs, Postgraduate Medicine*, 93(4):73–97 (1993).
http://www.natplus.com/products/productNumber=7124.
http://www.botanical.com/botanical/mgmh/f/franki31.html.
Cohen, et al. in *Wound Healing/Biochemical and Clinical Aspects*, 1st ed. WB Saunders, Philadelphia (1992).
Grindlay and Reynolds, *The Aloe Vera Phenomenon: A Review of the Properties and Modern Uses of the Leaf Parenchyma Gel*, (1986) J. of Ethnopharmacology, 16:117–151.
Hart, et al., *Two Functionally and Chemically Distinct Immunomodulatory Compounds in the Gel of Aloe Vera*, (1988) J. of Ethnopharmacology 23:61–71.
Hirata, et al., *Biologically Active Constituents of Leaves and Roots of Aloe Arborescens var. natalensis*, (1977) Z. Naturforsch, 32c:731–734.
Bronaugh and Collier, *In vitro Percutaneous absorption studies:Principle, Fundementals, and Applications*, eds. Bronaugh and Maibach, Boca Raton, Fl, CRC Press, pp237–241 (1991).
Nelson et al., *Mid–Infrared Laser Ablation of Stratum Corneum Enhances inVitro Percutaneous Transport of Drugs, The Society for Investigative Dermatology, Inc.* . . 874–879 (1991).
Collier et al., *Maintenace of Skin Viability during in Vitro Percuteneous Absorption/Metabolism Studies, Toxicology and Applied Pharmacology*, 99:522–533 (1989).
Barel and Clarys, *Study of the Stratum corneum Barrier Function by Transepidermal Water Loss Measurements: Comparison between Two Commercial Instruments, Skin Pharmacol.* 8:186–195 (1995).
Aloe Laboratories , *Manufacturing Procedures*, Product: Regular Traditional Hand Fillet Aloe Vera Juice, 1 page, date unknown.
Biomedical Information Services Ltd., *Inspection Criteria*, General Standard for Testing Purity of Aloe Vera 7 pages, Copyright 1996.
Chattem Inc., *Packaging—Flexall QuickGel*, Copyright 1999.
International Aloe Science Council, Inc., The, *Datasheet— 100*
Pure Aloe Vera., 1 page, date unknown.

*Primary Examiner*—Shelley A. Dodson
(74) *Attorney, Agent, or Firm*—Knobbe, Martens, Olson & Bear

(57) ABSTRACT

The present invention relates to the discovery of a transdermal delivery system that can deliver high molecular weight pharmaceuticals and cosmetic agents to skin cells. A novel transdermal delivery system with therapeutic and cosmetic application and methods of use of the foregoing is disclosed.

31 Claims, No Drawings

MIXTURE FOR TRANSDERMAL DELIVERY OF LOW AND HIGH MOLECULAR WEIGHT COMPOUNDS

RELATED APPLICATIONS

This application is a continuation of and claims priority to application Ser. No. 09/350,043 filed Jul. 8, 1999 now allowed, which claims priority U.S. Provisional Application Number 60/092,061, entitled EFFECTIVE PAIN RELIEF SOLUTION, filed Jul. 8, 1998 (now abandoned), all of which are hereby expressly incorporated by reference in their entireties.

FIELD OF THE INVENTION

The present invention relates to the discovery of a transdermal delivery system that can deliver high molecular weight pharmaceuticals and cosmetic agents to skin cells. A novel transdermal delivery system with therapeutic and cosmetic application and methods of use of the foregoing is disclosed.

BACKGROUND OF THE INVENTION

The skin provides a protective barrier against foreign materials and infection. In mammals this is accomplished by forming a highly insoluble protein and lipid structure on the surface of the corneocytes termed the cornified envelope (CE). (Downing et al., *Dermatology in General Medicine*, Fitzpatrick, et al., eds., pp. 210–221 (1993), Ponec, M., *The Keratinocyte Handbook*, Leigh, et al., eds., pp. 351–363 (1994)). The CE is composed of polar lipids, such as ceramides, sterols, and fatty acids, and a complicated network of cross-linked proteins; however, the cytoplasm of stratum corneum cells remains polar and aqueous. The CE is extremely thin (10 microns) but provides a substantial barrier. Because of the accessibility and large area of the skin, it has long been considered a promising route for the administration of drugs, whether dermal, regional, or systemic effects are desired.

A topical route of drug administration is sometimes desirable because the risks and inconvenience of parenteral treatment can be avoided; the variable absorption and metabolism associated with oral treatment can be circumvented; drug administration can be continuous, thereby permitting the use of pharmacologically active agents with short biological half-lives; the gastrointestinal irritation associated with many compounds can be avoided; and cutaneous manifestations of diseases can be treated more effectively than by systemic approaches. Most transdermal delivery systems achieve epidermal penetration by using a skin penetration enhancing vehicle. Such compounds or mixtures of compounds are known in the art as "penetration enhancers" or "skin enhancers". While many of the skin enhancers in the literature enhance transdermal absorption, several possess certain drawbacks in that (i) some are regarded as toxic; (ii) some irritate the skin; (iii) some on prolonged use have a thinning effect on the skin; (iv) some change the intactness of the skin structure, resulting in a change in the diffusability of the drug; and (v) all are incapable of delivering high molecular weight pharmaceuticals and cosmetic agents. Clearly there remains a need for safe and effective transdermal delivery systems that can administer a wide-range of pharmaceuticals and cosmetic agents to skin cells.

BRIEF SUMMARY OF THE INVENTION

In aspects of the invention described below, transdermal delivery systems are provided that can be used to administer pharmaceuticals and cosmetic agents of various molecular weights. In several embodiments, the transdermal delivery system comprises a novel formulation of penetration enhancer and aqueous adjuvant that enables the delivery of a wide range of pharmaceuticals and cosmetic agents having molecular weights of less than 100 daltons to greater than 500,000 daltons. For example, embodiments of the transdermal delivery system described herein can be used to deliver a therapeutically effective amount of a non-steroidal anti-inflammatory drug (NSAID), a capsaicin or Boswellin containing pain-relief solution, or several different collagen preparations. Methods of making and using the transdermal delivery devices of the invention for the treatment and prevention of human disease and cosmetic condition are also provided.

Accordingly, in one embodiment a transdermal delivery system is provided that comprises an ethoxylated lipid, an alcohol mixed with the ethoxylated lipid so as to form a penetration enhancer, an aqueous adjuvant mixed with the penetration enhancer, wherein the aqueous adjuvant is a plant extract from the family of Liliaceae, and a delivery agent mixed with the aqueous adjuvant and the penetration enhancer. In some aspects of this embodiment, the ethoxylated lipid is a vegetable or animal oil having at least 20 ethoxylations per molecule. In other aspects of this embodiment, about 0.1% to 40.0% by weight or volume is ethoxylated lipid. Other embodiments of the invention include the transdermal delivery system described above wherein about 0.1% to 15% by weight or volume is alcohol or wherein about 0.1% to 85% by weight or volume is *Aloe Vera*. Still more embodiments of the invention have a ratio of ethoxylated lipid:alcohol:aqueous adjuvant selected from the group consisting of 1:1:4, 1:1:14, 3:4:3, and 1:10:25.

Desirably, the transdermal delivery systems described above have delivery agents that are molecules having a molecular weight of less than 6,000 daltons. In some embodiments, the transdermal delivery system described above has a delivery agent that is one or more of the compounds selected from the group consisting of capsaicin, Boswellin, non steroidal anti-inflammatory drug, and collagen. Preferably, however, the delivery agent is a molecule having a molecular weight of greater than 6,000 daltons. Additional embodiments include an apparatus comprising a vessel joined to an applicator and the transdermal delivery system described above incorporated in the vessel. Applicators in embodiments of the invention can be a roll-on or a sprayer.

In another aspect, a transdermal delivery system is provided which comprises an ethoxylated oil, an alcohol mixed with the ethoxylated oil so as to form a penetration enhancer, an Aloe extract mixed with the penetration enhancer, and a therapeutically effective amount of capsaicin or NSAID or both mixed with the penetration enhancer and Aloe extract. In some embodiments of this aspect, the therapeutically effective amount of capsaicin is by weight or volume 0.01% to 5.0% capsaicin or 1.0% to 13% oleoresin capsicum. In other embodiments of this aspect, the transdermal delivery system further includes by weight or volume 0.1% to 10% Boswellin. As above, an apparatus having a vessel joined to an applicator that houses the transdermal delivery system is also an embodiment and preferred applicators include a roll-on or a sprayer.

Several methods are also within the scope of aspects of the invention. For example, one approach involves a method of reducing pain or inflammation comprising the step of administering the transdermal delivery system described above to a subject in need and monitoring the reduction in pain or inflammation. Additional methods of the invention include approaches to treat cancer and Alzheimer's disease. For example, a method of treating or preventing cancer and Alzheimer's disease can comprise the step of identifying a subject in need of a COX enzyme inhibitor and administering the transdermal delivery system described above to the subject.

In addition to the delivery of low and medium molecular weight delivery agents, several compositions that have high molecular weight delivery agents (e.g., collagens) and methods of use of such compositions are embodiments of the invention. For example, one embodiment concerns a transdermal delivery system comprising an ethoxylated oil, an alcohol mixed with the ethoxylated oil so as to form a penetration enhancer, an Aloe extract mixed with the penetration enhancer, and a therapeutically effective amount of collagen mixed with the penetration enhancer and Aloe extract.

In different embodiments of this transdermal delivery system, the collagen has a molecular weight less than 6,000 daltons or greater than 6,000 daltons. Thus, in certain embodiments, the collagen can have an approximate molecular weight as low as 2,000 daltons or lower. In a certain embodiment, the molecular weight is from about 300,000 daltons to about 500,000 daltons. Further, these transdermal delivery systems can have a therapeutically effective amount of collagen by weight or volume that is 0.1% to 50.0% and the collagen can be Hydrocoll EN-55 when the therapeutically effective amount by weight or volume is 0.1% to 50.0%; the collagen can be Solu-Coll when the therapeutically effective amount is 0.1% to 2.0%; and the collagen can be Plantsol when the therapeutically effective amount by weight or volume is 0.1% to 4.0%. As above, an apparatus having a vessel joined to an applicator that houses the transdermal delivery system is also an embodiment and preferred applicators include a roll-on or a sprayer.

Methods of reducing wrinkles and delivery of high molecular weight molecules are also embodiments of the invention. For example, by one approach, a method of reducing wrinkles in the skin comprises identifying a subject in need of skin tone restoration, administering the transdermal delivery system, such as is described above, to the subject and monitoring the restoration of skin tone. Further, methods of making a transdermal delivery system are within the scope of the invention. Accordingly, a method of making a transdermal delivery system can involve providing an ethoxylated oil, mixing the ethoxylated oil with an alcohol, nonionic solubilizer, or emulsifier so as to form a penetration enhancer, mixing the penetration enhancer with an aqueous adjuvant, wherein the aqueous adjuvant is an extract from a plant of the Liliaceae family; and mixing the penetration enhancer and aqueous adjuvant with a delivery agent and thereby making the transdermal delivery system.

In some aspects of this method, the delivery agent is selected from the group consisting of capsaicin, Boswellin, non steroidal anti-inflammatory drug, and collagen. In another embodiment of this method, the delivery agent has a molecular weight greater than 6,000 daltons. As above, an apparatus having a vessel joined to an applicator that houses the transdermal delivery system is also an embodiment and preferred applicators include a roll-on or a sprayer.

DETAILED DESCRIPTION OF THE INVENTION

In the following disclosure, several transdermal delivery systems are described that can administer an effective amount of a pharmaceutical or cosmetic agent to the human body. Although embodiments of the invention can be used to administer low or high (or both low and high) molecular weight pharmaceuticals and cosmetic agents, preferable embodiments include transdermal delivery systems that can administer compounds having molecular weights greater than 6,000 daltons. One embodiment, for example, includes a transdermal delivery system that can administer a therapeutically effective amount of a non-steroidal anti-inflammatory drug (NSAID). Another embodiment concerns a transdermal delivery system having a novel pain-relief solution (e.g., a formulation comprising capsaicin or Boswellin or both). Another aspect of the invention involves a transdermal delivery system that can administer a collagen preparation (e.g., soluble collagens, hydrolyzed collagens, and plant collagens). These examples are provided to demonstrate that embodiments of the invention can be used to transdermally deliver both low and high molecular weight compounds and it should be understood that many other molecules can be effectively delivered to the body, using the embodiments described herein, in amounts that are therapeutically, prophylactically, or cosmetically beneficial.

A transdermal delivery system has three components, a delivery agent, a penetration enhancer, and an aqueous adjuvant. Accordingly, one component of the transdermal delivery system of the invention is a "delivery agent". A molecule or a mixture of molecules (e.g., a pharmaceutical or cosmetic agent) that are delivered to the body using an embodiment of a transdermal delivery system of the invention are termed "delivery agents". A delivery agent that can be administered to the body using an embodiment of the invention can include, for example, a protein, a sugar, a nucleic acid, a chemical, or a lipid. Desirable delivery agents include, but are not limited to, glycoproteins, enzymes, genes, drugs, and ceramides. Preferred delivery agents include collagens, NSAIDS, capsaicin, and Boswellin. In some embodiments, a transdermal delivery system comprises a combination of the aforementioned delivery agents.

The second component of a transdermal delivery system is a penetration enhancer. Desirable penetration enhancers comprise both hydrophobic and hydrophilic components. The "hydrophobic component" includes one or more polyether compounds. One preferred polyether compound is an ethoxylated lipid. Although an ethoxylated lipid can be created in many ways, a preferred approach involves the reaction of ethylene oxide with a vegetable or animal oil. The "hydrophilic component" can be, for example, an alcohol, a nonionic solubilizer or an emulsifier. Suitable hydrophilic components include, but are not limited to, ethylene glycol, propylene glycol, dimethyl sulfoxide (DMSO), dimethyl polysiloxane (DMPX), oleic acid, caprylic acid, isopropyl alcohol, 1-octanol, ethanol (denatured or anhydrous), and other pharmaceutical grade or absolute alcohols with the exception of methanol.

Embodiments of the invention can also comprise a third component termed an "aqueous adjuvant". Aqueous adjuvants include, but are not limited to, water (distilled, deionized, filtered, or otherwise prepared), *Aloe Vera* juice, and other plant extracts. Thus, several embodiments of the invention have a penetration enhancer that includes a hydrophobic component comprising an ethoxylated oil (e.g., castor oil, glycerol, corn oil, jojoba oil, or emu oil) and a hydrophilic component comprising an alcohol, a nonionic solubilizer, or an emulsifier (e.g., isopropyl alcohol) and an aqueous adjuvant such as *Aloe Vera* extract. Other materials can also be components of a transdermal delivery system of the invention including fragrance, creams, ointments, colorings, and other compounds so long as the added component does not deleteriously affect transdermal delivery of the delivery agent. Unexpectedly, it has been found that compositions using extracts of plants of the Liliaceae family, such as *Aloe Vera*, provide superior benefits in transdermal delivery of high molecular weight delivery agents, including collagen having an average molecular weight greater than 6,000 daltons.

In addition to the aforementioned compositions, methods of making and using the embodiments of the invention are provided. In general, an embodiment of the invention is prepared by mixing a hydrophilic component with a hydrophobic component and an aqueous adjuvant. Depending on the solubility of the delivery agent, the delivery agent can be solubilized in either the hydrophobic, hydrophilic, or aqueous adjuvant components prior to mixing. In addition to physical mixing techniques (e.g., magnetic stirring or rocker stirring) heat can be applied to help coalesce the mixture. Desirably, the temperature is not raised above 40° C.

Several formulations of transdermal delivery system are within the scope of aspects of the invention. One formulation comprises a ratio of hydrophilic component:hydrophobic component:aqueous adjuvant of 3:4:3. The amount of delivery agent that is incorporated into the penetration enhancer depends on the compound, desired dosage, and application. The amount of delivery agent in a particular formulation can be expressed in terms of percentage by weight, percentage by volume, or concentration. Several specific formulations of delivery systems are provided in the Examples described herein.

Methods of treatment and prevention of pain, inflammation, and human disease are also provided. In some embodiments, a transdermal delivery system comprising an NSAID, capsaicin, Boswellin or any combination thereof is provided to a patient in need of treatment, such as for relief of pain and/or inflammation. The use of transdermal delivery systems described herein which contain extracts of the Liliaecae family, such as *Aloe Vera* extract, are particularly beneficial in the delivery of these delivery agents. A patient can be contacted with the transdermal delivery system and treatment continued for a time sufficient to reduce pain or inflammation or inhibit the progress of disease.

Additionally, a method of reducing wrinkles and increasing skin tightness and flexibility is provided. By this approach, a transdermal delivery system comprising a collagen delivery agent is provided to a patient in need, the patient is contacted with the transdermal delivery system, and treatment is continued for a time sufficient to restore a desired skin tone (e.g., reduce wrinkles or restore skin tightness and flexibility). The transdermal delivery system described herein provides unexpectedly superior results in the delivery of collagen of all molecular weights.

In the disclosure below, there is provided a description of several of the delivery agents that can be incorporated into the transdermal delivery devices of the present invention.
Delivery Agents Many different delivery agents can be incorporated into the various transdermal delivery systems of the invention and a non-exhaustive description of embodiments is provided in this section. While the transdermal delivery of molecules having a molecular weight in the vicinity of 6000 daltons has been reported, it has not been possible, until the present invention, to administer molecules of greater size transdermally. (U.S. Pat. No. 5,614,212 to D'Angelo et al.).

The described embodiments can be organized according to their ability to deliver a low or high molecular weight delivery agent. Low molecular weight molecules (e.g., a molecule having a molecular weight less than 6,000 daltons) can be effectively delivered using an embodiment of the invention and high molecular weight molecules (e.g., a molecule having a molecular weight greater than 6,000 daltons) can be effectively delivered using an embodiment of the invention. Desirably a delivery system of the invention can administer a therapeutically or cosmetically beneficial amount of a delivery agent having a molecular weight of 50 daltons to less than 6,000 daltons. Preferably, however, a delivery system of the invention can administer a therapeutically or cosmetically beneficial amount of a delivery agent having a molecular weight of 50 daltons to 2,000,000 daltons or less. That is, a preferred delivery system of the invention can administer a delivery agent having a molecular weight of less than or equal to 50, 100, 200, 500, 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 daltons.

In one aspect, a low molecular weight compound (e.g., a pain relieving substance or mixture of pain relieving substances) is transdermally delivered to cells of the body using an embodiment of a transdermal delivery system of the invention. The delivery agent can be, for example, any one or more of a number of compounds, including non-steroidal anti-inflammatory drugs (NSAIDs) that are frequently administered systemically. These include ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (-)); phenylbutazone (4-butyl-1,2-diphenyl-3,5-pyrazolidinedione); sulindac-(2)-5-fuoro-2-methyl-1-[[p-(methylsulfinyl)phenyl]methylene-]-1H-indene-3-acetic acid; diflunisal (2',4', -difluoro-4-hydroxy-3-biphenylcarboxylic acid; piroxicam (4-hydroxy-2-methyl-N-2-pyridinyl-2H-1, 2-benzothiazine-2-carboxamide 1, 1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl) amino]benzeneatic acid, monosodium salt); hydroxychloroquine sulphate (2-{[4-[(7-chloro-4-quinolyl) amino]pentyl] ethylamino}ethanol sulfate (1:1); penicillamine (3-mercapto-D-valine); flurbiprofen ([1,1-biphenyl]-4-acetic acid, 2-fluoro-alphamethyl-, (+-.)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N, N-di-methylethamine hydrochloride).

The delivery systems of the invention having NSAIDs desirably comprise an amount of the compound that is therapeutically beneficial for the treatment or prevention of disease or inflammation. Several studies have determined an appropriate dose of an NSAID for a given treatment or condition. (See e.g., Woodin, R N, August: 26–33 (1993) and Amadio et al., *Postgrduate Medicine*, 93(4):73–97 (1993)). The maximum recommended daily dose for several NSAIDs is listed in Table 1. The amount of NSAID recommended in the literature and shown in Table 1 can be incorporated into a delivery system of the invention. Because the transdermal delivery system of the invention can administer a delivery agent in a site-specific manner, it is believed that a lower total dose of therapeutic agent, as compared to the amounts provided systemically, will provide therapeutic benefit. Additionally, greater therapeutic benefit can be gained by using a transdermal delivery system of the invention because a high dose of therapeutic agent (e.g., an NSAID) can be applied to the particular site of inflammation. That is, in contrast to systemic administration, which applies the same concentration of therapeutic to all regions of the body, a transdermal delivery system of the invention can site-specifically administer a therapeutic and, thereby, provides a much greater regional concentration of the agent than if the same amount of therapeutic were administered systemically.

TABLE 1

| Agent | Maximum Recommended Daily Dose |
| --- | --- |
| Indomethacin | 100 mg |
| Ibuprofen | 3200 mg |
| Naproxen | 1250 mg |
| Fenoprofen | 3200 mg |
| Tolmetin | 2000 mg |
| Sulindac | 400 mg |
| Meclofenamate | 400 mg |
| Ketoprofen | 300 mg |
| Proxicam | 10 mg |
| Flurbiprofen | 300 mg |
| Diclofenac | 200 mg |

Additionally, desirable embodiments include a delivery system that can administer a pain relieving mixture comprising capsaicin (e.g., oleoresin capsicum) or Boswellin or both. Capsaicin (8-methyl-N-vanillyl-6-nonenamide), the pungent component of paprika and peppers, is a potent analgesic. (See U.S. Pat. Nos. 5,318,960 to Toppo, 5,885,597 to Botknecht et al., and 5,665,378 to Davis et al.). Capsaicin produces a level of analgesia comparable to morphine, yet it is not antagonized by classical narcotic antagonists such as naloxone. Further, it effectively prevents the development of cutaneous hyperalgesia, but appears to have minimal effects on normal pain responses at moderate doses. At high doses capsaicin also exerts analgesic activity in classical models of deep pain, elevating the pain threshold above the normal value. Capsaicin can be readily obtained by the ethanol extraction of the fruit of *Capsicum frutescens* or *Capsicum annum*. Capsaicin and analogs of capsaicin are available commercially from a variety of suppliers, and can also be prepared synthetically by published methods. Aspects of the invention encompass the use of synthetic and natural capsaicin, capsaicin derivatives, and capsaicin analogs.

A form of capsaicin used in several desirable embodiments is oleoresin capsicum. Oleoresin capsicum contains primarily capsaicin, dihydrocapsaicin, nordihydrocapsaicin, homocapsaicin, and homodihydrocapsaicin. The term "capsaicin" collectively refers to all forms of capsaicin, capsicum, and derivatives or modifications thereof. The pungency of these five compounds, expressed in Scoville units, are provided in Table 2.

TABLE 2

| Compound | Pungency × 100,000 SU |
| --- | --- |
| Capsaicin | 160 |
| Dihydrocapsaicin | 160 |
| Nordihydrocapsaicin | 91 |
| Homocapsaicin | 86 |
| Homodihydrocapsaicin | 86 |

The delivery systems of the invention having capsaicin desirably comprise by weight or volume 0.01% to 1.0% capsaicin or 1.0% to 10% oleoresin capsicum. Preferred amounts of this delivery agent include by weight or volume 0.02% to 0.75% capsaicin or 2.0% to 7.0% oleoresin capsicum. For example, the delivery systems of the invention having capsaicin can comprise by weight or volume less than or equal to 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% capsaicin. Although not a desirable embodiment, the delivery systems of the invention having capsaicin can comprise an amount of capsaicin by weight or volume that is greater than 1.0%, such as 1.2%, 1.5%, 1.8%, 2.0%, 2.2%, 2.5%, 2.8%, 3.0%, 3.5%, 4.0%, 4.5%, and 5.0%. Similarly, the delivery systems of the invention having oleoresin capsicum can comprise an amount of oleoresin capsicum less than 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 11.0%, 12.0%, and 13.0%.

Boswellin, also known as Frankincense, is an herbal extract of a tree of the Boswellia family. Boswellin can be obtained, for example, from *Boswellia thurifera, Boswellia carteri, Boswellia sacra*, and *Boswellia serrata*. There are many ways to extract Boswellin and Boswellin gum resin and boswellic acids are obtainable from several commercial suppliers (a 65% solution of Boswellic acid is obtainable from Nature's Plus over the internet at http://www.natplus.com/products/productNumber=7124). Some suppliers also provide creams and pills having Boswellin with and without capsaicin and other ingredients. (See e.g., http://www.preventics.com). Embodiments of the invention comprise Boswellin and the term "Boswellin" collectively refers to Frankincense, an extract from one or more members of the Boswellia family, Boswellic acid, synthetic Boswellin, or modified or derivatized Boswellin.

The delivery systems of the invention having Boswellin desirably comprise 0.1% to 10% Boswellin by weight or volume. Preferred amounts of this delivery agent include 1.0% to 5.0% Boswellin by weight. For example, the delivery systems of the invention having Boswellin can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, and 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4.0%, 4.1%, 4.15%, 4.2%, 4.25%, 4.3%, 4.35%, 4.4%, 4.45%, 4.4%, 4.45%, 4.5%, 4.55%, 4.6%, 4.65%, 4.7%, 4.75%, 4.8%, 4.85%, 4.9%, 4.95%, and 5.0% Boswellin. Although not a desirable embodiment, the delivery systems of the invention having Boswellin can comprise amounts of Boswellin by weight that are greater than 5.0%, such as 5.5%, 5.7%, 6.0%, 6.5%%, 6.7%, 7.0%, 7.5%, 7.7%, 8.0%, 8.5%, 8.7%, 9.0%, 9.5%, 9.7%, and 10.0% or greater. Additionally, Boswellin from different sources can be combined to compose the Boswellin component of an embodiment. For example, in one embodiment an extract from *Boswellia thurifera* is combined with an extract from *Boswellia serrata*.

Additional embodiments of the invention comprise a transdermal delivery system that can administer a pain relieving solution comprising two or more members selected from the group consisting of NSAIDs, capsacin, and Boswellin. The delivery systems of the invention that include two or more members selected from the group consisting of NSAIDs, capsacin, and Boswellin desirably comprise an amount of delivery agent that can be included in a delivery agent having an NSAID, capsaicin, or Boswellin by itself. For example, if the delivery agent comprises an NSAID, the amount of NSAID that can be used can be an amount recommended in the literature (See e.g., Woodin, R N, August: 26–33 (1993) and Amadio, et al., *Postgrduate Medicine,* 93(4):73–97 (1993)), or an amount listed in Table 1. Similarly, if capsaicin is a component of the delivery agents then the delivery system can comprise by weight or volume less than or equal to 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% capsaicin or less than 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 11.0%, 12.0%, 13.0%, oleoresin capsicum. Further, if Boswellin is a component of the delivery agents, then the delivery system can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4.0%,. 4.1%, 4.15%, 4.2%, 4.25%, 4.3%, 4.35%, 4.4%, 4.45%, 4.4%, 4.45%, 4.5%, 4.55%, 4.6%, 4.65%, 4.7%, 4.75%, 4.8%, 4.85%, 4.9%, 4.95%, 5.0%, 5.5%, 5.7%, 6.0%, 6.5%%, 6.7%, 7.0%, 7.5%, 7.7%, 8.0%, 8.5%, 8.7%, 9.0%, 9.5%, 9.7%, and 10.0% Boswellin.

In addition to low molecular weight delivery agents, many medium molecular weight delivery agents (eg., humates) can be delivered to cells in the body by using an embodiment of the transdermal delivery system. Synthetic humates ("Hepsyls") are medium molecular weight compounds (1,000 to 100,000 daltons), which are known to be strong antiviral and antimicrobial medicaments (International Application Publication No. WO 9834629 to Laub). Hepsyls are generally characterized as polymeric phenolic materials comprised of conjugated aromatic systems to which are attached hydroxyl, carboxyl, and other covalently bound functional groups. A delivery system that can administer Hepsyls to cells of the body has several pharmaceutical uses, including but not limited to, treatment of topical bacterial and viral infections.

Accordingly, in another aspect of the invention, a transdermal. delivery system that can administer a medium molecular weight compound (e.g., a form of Hepsyl) to cells of the body is provided. As described above, many different medium molecular weight compounds can be administered by using an embodiment of a transdermal delivery system of the invention and the use of a medium molecular weight Hepsyl as a delivery agent is intended to demonstrate that embodiments of the invention can deliver many medium molecular weight compounds to calls of the body.

In addition to low molecular weight delivery agents and medium molecular weight delivery agents, several high molecular weight delivery agents (e.g., glycoproteins) can be delivered to cells in the body by using an embodiment of the transdermal delivery system. Glycoproteins are high molecular weight compounds, which are generally characterized as conjugated proteins containing one or more heterosaccharides as prosthetic groups. The heterosaccharides are usually branched but have a relatively low number of sugar residues, lack a serially repeating unit, and are covalently bound to a polypeptide chain. Several forms of glycoproteins are found in the body. For example, many membrane bound proteins are glycoproteins, the substances that fill the intercellular spaces (e.g., extracellular matrix proteins) are glycoproteins, and the compounds that compose collagens, proteoglycans, mucopolysaccharides, glycosaminoglycans, and ground substance are glycoproteins. A delivery system that can administer glycoproteins to cells of the body has several pharmaceutical and cosmetic uses, including but not limited to, the restoration of skin elasticity and firmness (e.g., the removal of wrinkles by transdermal delivery of collagen) and the restoration of flexible and strong joints (e.g., water retention in joints can be increased by transdermal delivery of proteoglycans).

Accordingly, in another aspect of the invention, a transdermal delivery system that can administer a high molecular weight compound (e.g., a form of collagen) to cells of the body is provided. As described above, many different high molecular weight compounds can be administered by using an embodiment of a transdermal delivery system of the invention and the use of a high molecular weight collagen as a delivery agent is intended to demonstrate that embodiments of the invention can deliver many high molecular weight compounds to cells of the body.

Collagens exist in many forms and can be isolated from a number of sources. Additionally, several forms of collagen can be obtained commercially (e.g., Brooks Industries Inc., New Jersey). Many low molecular weight collagens can be made, for example, by hydrolysis. Several transdermal delivery systems of the invention can deliver collagens having molecular weights below 6,000 daltons. Additionally, several high molecular weight collagens exist. Some are isolated from animal or plant sources and some are synthesized or produced through techniques common in molecular biology. Several transdermal delivery systems of the invention can deliver collagens having molecular weights of 1,000 daltons to greater than 2,000,000 daltons. That is, embodiments of the transdermal delivery systems can deliver collagens having molecular weights of less than or equal to 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 daltons.

In some embodiments, the commercially available collagen "Hydrocoll EN-55" was provided as the delivery agent and was delivered to cells of a test subject. This form of collagen is hydrolyzed collagen and has a molecular weight of 2,000 daltons. In another embodiment, the commercially available collagen "Solu-Coll" was provided as the delivery agent and was delivered to cells of a test subject. This form of collagen is a soluble collagen having a molecular weight of 300,000 daltons. An additional embodiment includes the commercially available collagen "Plantsol", which is obtained from yeast and has a molecular weight of 500,000 daltons. This collagen was also provided as a delivery agent and was delivered to cells of a test subject.

The delivery systems of the invention having a form of collagen as a delivery agent desirably comprise by weight or volume between 0.1% to 50.0% collagen depending on the type of collagen, its solubility, and the intended application. That is, some transdermal delivery systems of the invention comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, or 50.0% collagen.

For example, embodiments having Hydrocoll-EN55 can comprise by weight or volume less than or equal to 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, or 50.0% Hydrocoll-EN-55. Further, delivery systems of the invention having Solu-Coll can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, or 2.0% Solu-Coll. Additionally, delivery systems of the invention having Plantsol can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, or 4.0% Plantsol.

In other embodiments of the invention, a transdermal delivery system that can administer a collagen solution comprising two or more forms of collagen (e.g., Hydro-Coll EN-55, Solu-coll, or Plantsol) is provided. The delivery systems of the invention that include two or more forms of collagen desirably comprise an amount of delivery agent that can be included in a delivery agent having the specific type of collagen by itself. For example, if the mixture of delivery agents comprises Hydro-Coll EN55, the amount of Hydro-Coll EN55 in the transdermal delivery system can comprise by weight or volume less than or equal to 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, or 50.0% Hydrocoll-EN-55. Similarly if the mixture of delivery agents have Solu-coll, then the amount of Solu-coll in the delivery device can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, or 2.0% or Solu-Coll. Further, if the mixture of delivery agents have Plantsol, then the amount of Plantsol in the delivery system can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, or 4.0% Plantsol.

In the section below, there is a description of the manufacture and use of a penetration enhancer that enables the delivery of both low and high molecular weight molecules to the skin cells of the body.

Penetration Enhancers

A penetration enhancer included in many embodiments of the invention is comprised of two components—a hydrophobic component and a hydrophilic component. Desirably, the hydrophobic component comprises a polyether compound, such as an ethoxylated vegetable or animal oil, that has the ability to reduce the surface tension of materials that are dissolved into it. Preferable ethoxylated oils can be obtained or created from, for example, castor oil, jojoba oil, corn oil, and emu oil. Desirably, the ethoxylated compound comprises at least 20–25 ethoxylations per molecule and preferably the ethoxylated compound comprises at least 30–35 ethoxylations per molecule. Thus, in a preferred embodiment, an ethoxylated oil comprises a molar ratio of ethylene oxide:oil of 35:1. A 99% pure ethylene oxide/castor oil having such characteristics can be obtained commercially (BASF) or such an ethoxylated compound can be synthesized using conventional techniques. Desirable compounds often found in ethoxylated oils that are beneficial for some embodiments and methods of the invention are glycerol-polyethylene glycol ricinoleate, the fatty esters of polyethylene glycol, polyethylene glycol, and ethoxylated glycerol. Some of these desirable compounds exhibit hydrophilic properties and the hydrophilic-lipophilic balance (HLB) is preferably maintained between 10 and 18. In some embodiments, more than one ethoxylated compound is added or another hydrophobic compound is added (e.g., Y-Ling-Y-Lang oil; Young Living Essential Oils, Lehl, Utah)) to balance or enhance the penetration enhancer.

Depending on the type of delivery agent and the intended application, the amount of ethoxylated lipid(s) in the delivery system can vary. For example, delivery systems of the invention can comprise between 0.1% and 40% by weight or volume ethoxylated compound(s). That is, embodiments of the invention can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, and 40.0% ethoxylated lipid(s).

The hydrophilic component of the penetration enhancers of the invention desirably comprise an alcohol, a non-ionic solubilizer, or an emulsifier. Compounds such as ethylene glycol, propylene glycol, dimethyl sulfoxide (DMSO), dimethyl polysiloxane (DMPX), oleic acid, caprylic acid, isopropyl alcohol, 1-octanol, ethanol (denatured or anhydrous), and other pharmaceutical grade or absolute alcohols with the exception of methanol can be used. Preferred embodiments comprise an alcohol (e.g., absolute isopropyl alcohol), which is commercially available. As above, the amount of hydrophilic component in the penetration enhancer depends on the type of the delivery agent and the intended application. The hydrophilic component of a penetration enhancer of the invention can comprise between 0.1% and 50% by weight or volume. That is, a delivery system of the invention can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, or 50.0% hydrophilic component.

In addition to the delivery agent and penetration enhancer, desirable transdermal delivery devices comprise a third component—an aqueous adjuvant. In the section below, there is described the manufacture and use of a preferred aqueous adjuvant, *Aloe Vera*, that enhances the delivery of both low and high molecular weight molecules to the skin cells of the body.

Aqueous Adjuvants

The term "Aloe" refers to the genus of South African plants of the Liliaceae family, of which the *Aloe barbadensis* plant is a species. Aloe is an intricate plant, which contains many biologically active substances. (Cohen, et al. in Wound Healing/Biochemical and Clinical Aspects, 1st ed. W B Saunders, Philadelphia (1992)). Over 300 species of Aloe are known, most of which are indigenous to Africa. Studies have shown that the biologically active substances are located in three separate sections of the Aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart, et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity, (See e.g., Yagi, et al. (1977) Z. Naturforsch. 32c:731–734), and antioxidant activity (International Application Serial No. PCT/US95/07404). Recent research has also shown that *Aloe Vera*, a term used to describe the extract obtained from processing the entire leaf, isolated from the *Aloe Vera* species of Aloe, can be used as a vehicle for delivering hydrocortisone, β-estradiol, and testosterone propionate. (Davis, et al, *JAPMA* 81:1 (1991) and U.S. Pat. No. 5,708,038 to Davis)). As set forth in Davis (U.S. Pat. No. 5,708,308), one embodiment of "*Aloe Vera*" can be prepared by "whole-leaf processing" of the whole leaf of the *Aloe barbadensis* plant. Briefly, whole leaves obtained from the *Aloe barbadensis* plant are ground, filtered, treated with cellulase (optional) and activated carbon and lyophilized. The lyophilized powder is then reconstituted with water prior to use.

In some embodiments, Aloe Vera is commercially available and obtained through Aloe Laboratories. In some embodiments, the Aloe Vera is manufactured by manually harvesting the Aloe leaves. Next, the leaves are washed with water and the thorns on both ends are cut. The leaves are then hand-filleted so as to extract the inner part of the leaf. The inner gel is passed through a grinder and separator to remove fiber from the gel. Next, the gel is put into a pasteurizing tank where L-Ascorbic Acid (Vitamin C) and preservatives are added. The gel is pasteurized at 85° C. for 30 minutes. After pasteurization, the gel is put into a holding tank for about one or two days, after which the gel is sent through a ½ micron filter. Finally, the gel is cooled down through a heat exchanger and stored in a steamed, sanitized and clean 55 gallon drum.

The above described sources and manufacturing methods of Aloe Vera are given as examples and not intended to limit the scope of the invention. One of ordinary skill in the art will recognize that Aloe Vera is a well known term of art, and that Aloe Vera is available from various sources and manufactured according to various methods.

Several embodiments of the invention are comprised of aqueous adjuvants such as Aloe Vera juice or water or both. Absolute Aloe Vera (100% pure) can be obtained from commercial suppliers (Lily of the Desert, Irving, Tex.). Aloe Vera juice, prepared from gel fillet, has an approximate molecular weight of 200,000 to 1,400,000 daltons. Whole leaf Aloe Vera gel has a molecular weight of 200,000 to 3,000,000 depending on the purity of the preparation. Although, preferably, the embodiments of the invention having Aloe Vera comprise Aloe Vera juice, other extracts from a member of the Liliaceae family can be used (e.g., an extract from another Aloe species).

Transdermal delivery systems of the invention having Aloe Vera can comprise between 0.1% to 85.0% by weight or volume Aloe Vera. That is, embodiments of the invention can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%,. 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%,. 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.25%, 40.5%, 40.75%, 41.0%, 41.25%, 41.5%, 41.75%, 42.0%, 42.25%, 42.5%, 42.75%, 43.0%,. 43.25%, 43.5%, 43.75%, 44.0%, 44.25%, 44.5%, 44.75%, 45.0%, 45.25%, 45.5%, 45.75%, 46.0%, 46.25%, 46.5%, 46.75%, 47.0% 47.25%, 47.5%, 47.75%, 48.0%, 48.25%, 48.5%, 48.75%, 49.0%, 49.25%, 49.5%, 49.75%, 50.0%,. 50.25%, 50.5%, 50.75%, 51.0%, 51.25%, 51.5%, 51.75%, 52.0%, 52.25%, 52.5%, 52.75%, 53.0%, 53.25%, 53.5%, 53.75%, 54.0%, 54.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81%, 81.5%, 82%, 82.5%, 83%, 83.5%, 84%, 84.5%, and 85% Aloe Vera.

The amount of water in the delivery system generally depends on the amount of other reagents (e.g., delivery agent, penetration enhancer, and other aqueous adjuvants or fillers). Although water is used as the sole aqueous adjuvant in some embodiments, preferred embodiments use enough water to make the total volume of a particular preparation of a delivery system such that the desired concentrations of reagents in the penetration enhancer, aqueous adjuvant, and delivery agent are achieved. Suitable forms of water are deionized, distilled, filtered or otherwise purified. Clearly, however, any form of water can be used as an aqueous adjuvant.

In addition to the aforementioned compositions, methods of making and using the transdermal delivery systems of the invention are provided below.

Preparing Transdermal Delivery Systems

In general, an embodiment of the invention is prepared by combining a penetration enhancer with an aqueous adjuvant and a delivery agent. Depending on the solubility of the delivery agent, the delivery agent can be solubilized in either the hydrophobic or hydrophilic components of the penetration enhancer. Additionally, some delivery agents can be solubilized in the aqueous adjuvant prior to mixing with the penetration enhancer. Desirably, the pH of the mixture is maintained between 3 and 11 and preferably between 5 and 9. That is, during preparation and after preparation the pH of the solution is desirably maintained at less than or equal to 3.0, 3.25, 3.5, 3.75, 4.0, 4.25, 4.5, 4.75, 5.0, 5.25, 5.5, 5.75, 6, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, or 11.0. Several physical mixing techniques can be employed to help the delivery system coalesce. For example, a magnetic stir plate and bar can be used, however, the speed of stirring is preferably minimized so as not to drive air into the mixture. Additionally, a rocker can be used to bring components of the delivery system together. Heat can also be applied to help coalesce the mixture but desirably, the temperature is not raised above 40° C. so that labile aqueous adjuvants or labile delivery agents are not degraded. Preferably, once the delivery system has coalesced, other components such as fragrances and colors are added or the delivery system is incorporated into a cream or ointment or a device for applying the delivery system.

Several formulations of delivery system are within the scope of aspects of the invention. Desirably, the ratio of hydrophilic component:hydrophobic component:aqueous adjuvant is 3:4:3, but preferred formulations comprise 1:1:4, 1:1:14, and 1:10:25. As described above, a sufficient amount of delivery agent to suit the intended purpose is incorporated into the delivery system. The amount of delivery agent that is incorporated into the penetration enhancer depends on the compound, desired dosage, and application.

Typically, a preferable transdermal delivery system is made by providing an ethoxylated oil, mixing the ethoxylated oil with an alcohol, non-ionic solubilizer, or emulsifier so as to form a penetration enhancer, mixing the penetration enhancer with an aqueous adjuvant (e.g., an extract from a plant of the Liliaeacae family), and mixing the penetration enhancer and aqueous adjuvant with a delivery agent and thereby making the transdermal delivery system. For example, an embodiment of a transdermal delivery system comprising a pain relief solution is manufactured as follows. A solution of 2.0% to 7.0% oleoresin capsicum, 2.5 grams of Boswellin, and 1.5 mls of a 65% solution of Frankensence is mixed with 400 ml of absolute carpilic alcohol or isopropyl alcohol, 300 ml of ethylene oxide admixed and reacted with castor oil, and 300 ml of a 100% solution of *Aloe Vera*. This transdermal delivery system has been observed to alleviate pain when rubbed on a targeted area.

The delivery systems of the invention having a form of Hepsyl as a delivery agent desirably are comprised by weight or volume of between 0.005% to 12.0% Hepsyl, depending on the type of Hepsyl, its solubility, and the intended application. For example, embodiments having Hepsyl CA 1501C. Hepsyl CGA 1501K., and Hepsyl RA 150K can be comprised by weight or volume of 0.01–2 grams of Hepsyl delivery agent, 0–50 mL of hydrophobic penetration enhancers (e.g., ethoxylated castor oil, jojoba oil, etc.), 0–50 mL of hydrophilic penetration enhancers, nonionic solubilizers, or emulsifiers (e.g., isopropyl. alcohol, DMSO, etc.), and 0–50 mL of aqueous adjuvant (e.g., water, *Aloe Vera* extract, etc.). A particularly desirable embodiment of the invention is comprised of 0.1–0.5 gram of Hepsyl, 5–10 mL of ethoxylated castor oil, 5–10 mL of isopropyl alcohol, and 5–10 mL of *Aloe Vera* extract. By using these formulations, other delivery agents can incorporated into a transdermal delivery system. Formulations of transdermal delivery systems having collagens are described in Example 2.

In the disclosure below, several therapeutic, prophylactic and cosmetic applications are provided.

Therapeutic, Prophylactic, and Cosmetic Applications

Many embodiments are suitable for treatment of subjects either as a preventive measure (e.g., to avoid pain or skin disorders) or as a therapeutic to treat subjects already afflicted with skin disorders or who are suffering pain. In one embodiment, a method of treatment or prevention of inflammation, pain, or human diseases, such as cancer, arthritis, and Alzheimer's disease, comprises using a transdermal delivery system of the invention. Because delivery agents such as NSAIDs, capsaicin, and Boswellin interfere and/or inhibit cyclooxygenase enzymes (COX-1 and COX-2), they will provide a therapeutically beneficial treatment for cancer and Alzheimer's disease when administered by a transdermal delivery system of the invention. (U.S. Pat. No. 5,840,746 to Ducharme et al., and U.S. Pat. No. 5,861,268 to Tang et al.).

By one approach, a transdermal delivery system comprising a delivery agent that is effective at reducing pain or inflammation (e.g., NSAIDS, capsaicin, Boswellin, or any combination thereof) is administered to a subject in need and the reduction in pain or inflammation is monitored. An additional approach involves identifying a subject in need of a COX enzyme inhibitor (e.g., a subject suffering from cancer or Alzheimer's disease) and administering a transdermal delivery system comprising a delivery agent that inhibits a COX enzyme (e.g., NSAIDS, capsaicin, Boswellin, or any combination thereof). Although many individuals can be at risk for contracting cancer or Alzheimer's disease, those with a family history or a genetic marker associated with these maladies are preferably identified. Several diagnostic approaches to identify persons at risk of developing these diseases have been reported. (See e.g., U.S. Pat. Nos., 5,891,857; 5,744,368; 5,891,651; 5,837,853; and 5,571,671). The transdermal delivery system is preferably applied to the skin at a region of inflammation or an area associated with pain or the particular condition and treatment is continued for a sufficient time to reduce inflammation, pain, or inhibit the progress of the disease. Typically, pain and inflammation will be reduced in 5–20 minutes after application. Cancer and Alzheimer's disease can be inhibited or prevented with prolonged use.

In another method of the invention, an approach to reduce wrinkles and increase skin tightness and flexibility (collectively referred to as "restoring skin tone") is provided. Accordingly, a transdermal delivery system comprising a form of collagen as a delivery agent is provided and contacted with the skin of a subject in need of treatment. By one approach, a subject in need of skin tone restoration is identified, a transdermal delivery system comprising collagen is administered to the subject, and the restoration of the skin tone is monitored. Identification of a person in need of skin restoration can be based solely on visible inspection and the desire to have tight, smooth, and flexible skin. Treatment with the delivery system is continued until a desired skin tone is achieved. Typically a change in skin tone will be visibly apparent in 15 days but prolonged use may be required to retain skin tightness and flexibility. The form of collagen in the delivery agent can be from various sources and can have many different molecular weights, as detailed above. Preferably, high molecular weight collagens are used.

The transdermal delivery systems of this invention can be processed in accordance with conventional pharmacological and cosmetological methods to produce medicinal agents and cosmetics for administration to patients, e.g., mammals including humans. The transdermal delivery systems described herein can be incorporated into a pharmaceutical or cosmetic product with or without modification. The compositions of the invention can be employed in admixture with conventional excipients, e.g., pharmaceutically acceptable organic or inorganic carrier substances suitable for topical application that do not deleteriously react with the molecules that assemble the delivery system. The preparations can be sterilized and if desired mixed with auxiliary agents, e.g., lubricants, preservatives, stabilizers, coloring, aromatic substances and the like that do not deleteriously react with the active compounds. They can also be combined where desired with other active agents.

The effective dose and method of administration of a carrier system formulation can vary based on the individual patient and the stage of the disease, as well as other factors known to those of skill in the art. Although several doses of delivery agents have been indicated above, the therapeutic efficacy and toxicity of such compounds in a delivery system of the invention can be determined by standard pharmaceutical or cosmetological procedures with experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical and cosmetological compositions that exhibit large therapeutic indices are preferred. The data obtained from animal studies is used in formulating a range of dosages for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the delivery systems of the invention are primarily topical, although it is desired to administer some embodiments to cells that reside in deep skin layers. Topical administration is accomplished via a topically applied cream, gel, rinse, etc. containing a delivery system of the invention. Compositions of delivery system-containing compounds suitable for topical application include, but are not limited to, physiologically acceptable ointments, creams, rinses, and gels.

In some embodiments, the mixture of penetration enhancer, aqueous adjuvant, and delivery agent is incorporated into a device that facilitates application. These apparatus generally have a vessel joined to an applicator, wherein a transdermal delivery system of the invention is incorporated in the vessel. Some devices, for example, facilitate delivery by encouraging vaporization of the mixture. These apparatus have a transdermal delivery system of the invention incorporated in a vessel that is joined to an applicator such as a sprayer (e.g., a pump-driven sprayer). These embodiments can also comprise a propellant for driving the incorporated transdermal delivery system out of the vessel. Other apparatus can be designed to allow for a more focused application. A device that facilitates a focused application of a transdermal delivery system of the invention can have a roll-on or swab-like applicator joined to the vessel that houses the transdermal delivery system. Several devices that facilitate the administration of a delivery system of the invention have a wide range of cosmetic or therapeutic applications.

In the example below a clinical study is described that was performed to evaluate the efficacy of a transdermal delivery system that administered a low molecular weight pain relief solution comprising capsaicin.

EXAMPLE 1

In this example, evidence is provided that a transdermal delivery system of the invention can administer a therapeutically effective amount of a low molecular weight delivery agent (e.g., 0.225% oleoresin capsicum). A clinical study was performed to evaluate the effectiveness of a transdermal delivery system of the invention comprising 0.225% capsaicin ("EPRS") as compared to a commercially available cream comprising Boswellin, 10% methyl salicylate, and 0.25% capsaicin. (Nature's Herbs). The two pain relief preparations were tested on six subjects who suffer from degenerative arthritis, debilitating back pain, and/or bursitis. For the first five days of the study, the subjects applied the commercially available cream three times a day. On day six, application of the commercially available cream was stopped and subjects applied the EPRS transdermal delivery system. The EPRS pain relief solution was also applied for five days, three times a day. Daily analysis of the efficacy of the particular pain relief formulations was taken by the subjects and observations such as the time of administration, odor, and therapeutic benefit were recorded after each administration.

The five day use of the commercially available cream was found to provide only minimal therapeutic benefit. The cream was reported to irritate the skin, have a noxious smell, and provide little decrease in pain or increase in flexibility or range of motion. In contrast, the five day use of EPRS was reported to provide significant pain relief, relative to the relief obtained from the oral consumption of NSAIDs. Further, EPRS was reported to increase flexibility and range of motion within five to twenty minutes after application. Additionally, EPRS did not present a significant odor nor did it cause skin irritation. The results of this study demonstrate that a delivery system comprising a low molecular weight compound, capsaicin, can effectively administer the delivery agent to cells of the body where it provides therapeutic benefit.

In the example below, a clinical study is described that was performed to evaluate the efficacy of a transdermal delivery system that administered low and high molecular weight collagens.

EXAMPLE 2

In this example, evidence is provided that a transdermal delivery system of the invention can administer a therapeutically effective amount of a low and high molecular weight delivery agent (e.g., a low and high molecular weight collagen). A clinical study was performed to evaluate the effectiveness of several transdermal delivery systems of the invention comprising various penetration enhancers, aqueous adjuvants, and collagen delivery agents. The various transdermal delivery systems that were evaluated are provided in Table 3. Of the formulations that were originally screened, three were extensively evaluated by ten subjects (three men and seven women) in a single blind study. The formulations analyzed in the single blind study are indicated in Table 3 by a dagger. That is, the three different formulations ("P1", "P2", and "F4") were evaluated.

The P1 formulation comprised approximately 0.73% to 1.46% Solu-Coll, a soluble collagen having a molecular weight of 300,000 daltons. The P2 formulation comprised approximately 1.43% to 2.86% Plantsol, a plant collagen obtained from yeast having a molecular weight of 500,000 daltons. The F4 formulation comprised approximately 11.0% of HydroColl EN-55, a hydrolyzed collagen having a molecular weight of 2,000 daltons. The evaluation of the P1, P2, and F4 formulations was as follows. Left, right, and center mug-shot photographs were taken with a Pentax camera having a zoom 60X lens and Kodak-Gold 100 film before beginning the study. Shortly after, each subject was given a bottle having a formulation of transdermal delivery system and was instructed to apply the solution to the right side of the face and neck, leaving the left side untreated, twice daily for 15 days. The F4 formulation was tested first and the application was carried out after showering or washing and before application of any other product to the treated area of the face. After the 15 day period, three mug-shot photographs were again taken, the subjects recorded their observations on the effectiveness of the formulation in a questionnaire, and a 7 day period without application of a collagen product provided. The questionnaire requested the subject to assign a score (e.g., a numerical value that represents effectiveness) on characteristics of the transdermal delivery system formulation. Characteristics that were evaluated included tackiness, odor, marketability, and overall effectiveness of the formulation, as well as, whether the formulation tightened the skin, decreased lines, conditioned or softened the skin, and had any negative side-effects. The scale for the scoring was 1–10, with 1 being the worst rating and 10 being the best rating.

Following the test of F4, the evaluation detailed above was conducted on the P1 formulation. Again, photographs were taken before and after the second 15 day protocol, a questionnaire evaluating the efficacy of the particular formulation was completed, and a 7 day period without application of a collagen product was provided. Further, after the test of P1, the same evaluation was conducted on the P2 formulation, photographs were taken before and after the trial, and a questionnaire evaluating the efficacy of the particular formulation was completed.

The data from the three evaluation questionnaires were pooled, analyzed using a "t-table" and standard deviation calculations were made. See Table 4. An overall rating for each particular formulation was assigned. A perfect score by this system was a 7.875 overall rating. P1 was found to have a 4.25 overall rating (approximately 54% effective), P2 was found to have a 4.625 overall rating (approximately 59% effective), and F4 was found to have a 5.625 overall rating (approximately 71% effective).

The before and after treatment photographs also revealed that the three tested transdermal delivery systems provided therapeutic benefit. A decrease in wrinkles was observed and an increase in skin tightness and firmness can be seen. That is, P1, P2, and F4 all provided therapeutic and/or cosmetic benefit in that they restored skin tone in the subjects tested. The results presented above also demonstrate that transdermal delivery systems of the invention can be used to administer high molecular weight delivery agents.

TABLE 4-continued

Collagen T-Table

| Formulations | P1 | P2 | P4 | standard deviation |
|---|---|---|---|---|
| Total skin restoration | 5 | 5 | 6 | 0.47 |
| Market Buying Power | 5 | 7 | 8 | 1.25 |
| Side effects | 0 | 0 | 0 | 0 |
| Total Score (Average) | 4.25 | 4.63 | 5.63 | 1.36 |

Several in vitro techniques are now widely used to assess the percutaneous absorption of delivery agents. (See e.g., Bronaugh and Collier in *In vitro Percutaneous absorption studies:Principle, Fundamentals, and Applications*, eds. Bronaugh and Maibach, Boca Raton, Fla., CRC Press, pp237–241 (1991) and Nelson et al., *J. Invest. Dermatol.* 874–879 (1991), herein incorporated by reference). Absorption rates, and skin metabolism can be studied in viable skin without the interference from systemic metabolic processes. In the example below, several approaches are described that can be used to evaluate the administration of a delivery agent by using a transdermal delivery system of the invention.

EXAMPLE 3

Skin barrier function can be analyzed by examining the diffusion of fluorescent and colored proteins and dextrans of

TABLE 3

| ECO | Aloe | IPA | Plantsol | EN-55 | Solucoll | DMPX | YYO | Score | ID |
|---|---|---|---|---|---|---|---|---|---|
| 29.7%* | 50.0%* | 5.0%* | 0* | 8.3%* | 0* | 0* | 0* | 2 | F-1 |
| 10.4% | 79.0% | 5.3% | 0 | 8.7% | 0 | 0 | 0 | 3 | F-2 |
| 5.2% | 63.0% | 5.3% | 0 | 17.4% | 0 | 0 | 0 | 3 | F-3 |
| 5.0% | 70.0% | 5.0% | 0 | 11.0% | 0 | 0 | 0 | 3+ | F-4† |
| 4.5% | 18.2% | 4.6% | 0 | 0 | 0.7% to 1.5% | 0 | 0 | 3+ | P-1† |
| 8.3% | 8.3% | 8.3% | 0.7% to 1.4% | 4.6% | 0.3% to 0.7% | 0 | 0 | 2 | Y-500 |
| 0.7% | 22.2% | 11.1% | 1.3% to 2.7% | 0 | 0 | 0 | 0 | 3+ | P-501 |
| 0.4% | 35.7% | 3.6% | 1.1% to 2.1% | 0 | 0 | 0 | 0 | 2 | P-502 |
| 0.9% | 8.7% | 0 | 0 | 0 | 2.3% to 4.6% | 0 | 0 | 1 | SC-1 |
| 1.8% | 18.5% | 0 | 0 | 44.8% | 0 | 0 | 0 | 3+ | SC-2 |
| 1.8% | 17.9% | 7.1% | 0 | 43.2% | 0 | 0 | 0 | 3 | SC-3 |
| 0.9% | 9.4% | 4.7% | 0 | 34.3% | 0.3% to 0.6% | 0 | 0 | 1 | PSCEN |
| 1.8% | 31.3% | 6.3% | 1.3% to 2.5% | 0 | 0 | 0 | 0 | 3+ | P-1A |
| 0.8% | 19.2% | 3.8% | 1.5% to 3.1% | 0 | 0 | 7.7% | 0.3% | 5 | P-1C |
| 0.7% | 17.9% | 7.1% | 1.4% to 2.9% | 0 | 0 | 1.1% | 0.3% | 5 | P-2† |
| 0.7% | 22.2% | 11.1% | 1.3% to 2.7% | 0 | 0 | 0 | 0 | 3+ | P-501 |

Abbreviations:
ECO - ethoxylated castor oil (BASF)
Aloe - Aloe Vera (Aloe Labs; (800)-258-5380)
IPA - Absolute isopropyl alcohol (Orange County Chemical, Santa Ana, California)
Plantsol - Yeast extract collagen (Brooks Industries Inc., Code No. 06485)
EN-55 - hydrolyzed bovine collagen (Brooks Industries Inc., Code No. 01000)
SoluColl - soluble collagen (Brooks Industries Inc., Code No. 01029)
DMPX - dimethyl polysiloxane (5 centistokes) (Sigma)
YYU - Y-ling-Y-lang oil (Young Living Essential Oils, Lehl, Utah)
ID - Identification number
*The percentages reflect volume to volume.
†Sample used in the 45 day clinical trial.

TABLE 4

Collagen T-Table

| Formulations | P1 | P2 | P4 | standard deviation |
|---|---|---|---|---|
| Tackiness | 5 | 3 | 10 | 2.94 |
| Skin tightness | 7 | 5 | 8 | 1.25 |
| Odor | 2 | 8 | 8 | 2.83 |
| Decrease lines | 2 | 2 | 1 | 0.47 |
| Soften skin | 8 | 7 | 4 | 1.7 | various molecular weights ("markers") across the skin of nude mice or swine. Swine skin is preferred for many studies because it is inexpensive, can be maintained at −20° C., and responds similarly to human skin. Prior to use, frozen swine skin is thawed, hair is removed, and subcutaneous adipose tissue is dissected away. Preferably, a thickness of skin that resembles the thickness of human skin is obtained (e.g., several millimeters) so as to prepare a membrane that accurately reflects the thickness of the barrier layer. A dermatome can be pushed across the surface of the skin so as to remove any residual dermis and prepare a skin preparation that accurately reflects human skin. Elevation of temperature can also be used to loosen the bond between the dermis and the epidermis of hairless skin. Accordingly, the excised skin is placed on a hot plate or in heated water for 2 minutes at a temperature of approximately 50° C.–60° C. and the dermis is removed by blunt dissection. Chemical approaches (e.g., 2M salt solutions) have also been used to separate the dermis from the epidermis of young rodents.

Many different buffers or receptor fluids can be used to study the transdermal delivery of delivery agents across excised skin prepared as described above. Preferably, the buffer is isotonic, for example a normal saline solution or an isotonic buffered solution. More physiological buffers, which contain reagents that can be metabolized by the skin, can also be used. (See e.g., Collier et al., *Toxicol. Appl. Pharmacol.* 99:522–533 (1989)).

Several different markers with molecular weight from 1,000 daltons to 2,000,000 daltons are commercially available and can be used to analyze the transdermal delivery systems of the invention. For example, different colored protein markers having a wide range of molecular weights (6,500 to 205,000 daltons) and FITC conjugated protein markers (e.g., FITC conjugated markers from 6,500 to 205,000 daltons) are available from Sigma (C3437, M0163, G7279, A2065, A2190, C1311, T9416, L8151, and A2315). Further, high molecular weight FITC conjugated dextrans (e.g., 250,000, 500,000, and 2,000,000 daltons) are obtainable from Sigma. (FD250S, FD500S, and FD2000S).

Accordingly, in one approach, swine skin preparations, obtained as described above, are treated with a delivery system lacking a delivery agent and control swine skin preparations are treated with water. Subsequently, the skin is contacted with a 1 mM solution of a marker with a known molecular weight suspended in Ringer's solution (pH 7.4) at 37° C. After one hour, the skin is frozen and sliced at a thickness of 5 $\mu$m. The sections are counter stained with 5 $\mu$g/ml propidium iodide and, if the marker is FITC conjugated, the sections are analyzed by fluoresence microscopy. If the marker is a colored marker, diffusion of the marker can be determined by light microscope. The marker will be retained in the upper layers of the stratum corneum in the untreated mice but the delivery system treated mice will be found to have the dye distributed throughout the stratum corneum and any dermal layer that remains.

Additionally, modifications of the experiments described above can be performed by using a delivery system comprising various molecular weight markers. Accordingly, skin preparations are treated with the delivery system comprising one or more markers and control skin preparations are treated with water. After one hour, the skin is frozen and sliced at a thickness of 5 $\mu$m. The sections can be counter stained with 5 $\mu$g/ml propidium iodide and can be analyzed by fluoresence microscopy (e.g., when a fluorescent marker is used) or alternatively, the sections are analyzed under a light microscope. The various markers will be retained in the upper layers of the stratum corneum in the untreated mice but the delivery system treated mice will be found to have the marker distributed throughout the stratum corneum and any dermal layer that remains.

In another method, the transdermal water loss (TEWL) of penetration enhancer-treated skin preparations can be compared to that of untreated skin preparations. Accordingly, skin preparations are obtained, as described above, and are treated with a delivery system of the invention lacking a delivery agent (e.g., a penetration enhancer). Control skin preparations are untreated. To assess TEWL, an evaporimeter is used to analyze the skin preparation. The Courage and Khazaka Tewameter TM210, an open chamber system with two humidity and temperature sensors, can be used to measure the water evaporation gradient at the surface of the skin. The parameters for calibrating the instrument and use of the instrument is described in Barel and Clarys *Skin Pharmacol.* 8: 186–195 (1995) and the manufacturer's instructions. In the controls, TEWL will be low. In contrast, TEWL in penetration enhancer-treated skin preparations will be significantly greater.

Further, skin barrier function can be analyzed by examining the percutaneous absorption of labeled markers (e.g., radiolabeled, fluorescently labeled, or colored) across skin preparations in a diffusion chamber. Delivery systems of the invention having various molecular weight markers, for example, the proteins and dextrans described above, are administered to swine skin preparations. Swine skin preparations are mounted in side-by-side diffusion chambers and are allowed to stabilize at 37° C. with various formulations of penetration enhancer. Donor and receiver fluid volumes are 1.5 ml. After 1 hour of incubation, a labeled marker is added to the epidermal donor fluid to yield a final concentration that reflects an amount that would be applied to the skin in an embodiment of the invention. Five hundred $\mu$l of receiver fluid is removed at various time points, an equal volume of penetration enhancer is added to the system. The aliquot of receiver fluid removed is then analyzed for the presence of the labeled marker (e.g., fluorescent detection, spectroscopy, or scintillation counting). Control swine skin preparations are equilibrated in Ringer's solution (pH 7.4) at 37° C.; the same concentration of labeled marker as used in the experimental group is applied to the donor fluid after one hour of equilibration; and 500 $\mu$l of receiver fluid is analyzed for the presence of the marker. In the experimental group, the steady-state flux of labeled marker in the skin will be significantly greater than that of the control group.

By using these approaches, several transdermal delivery systems can be evaluated for their ability to transport low and high molecular weight delivery agents across the skin.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A transdermal delivery system comprising:
   an ethoxylated oil;
   an alcohol mixed with the ethoxylated oil so as to form a penetration enhancer;
   an aqueous adjuvant mixed with the penetration enhancer; and
   a delivery agent mixed with the aqueous adjuvant and the penetration enhancer.

2. The transdermal delivery system of claim 1, wherein said aqueous adjuvant comprises *Aloe vera*.

3. The transdermal delivery system of claim 1, wherein said aqueous adjuvant comprises water.

4. The transdermal delivery system of claim 1, wherein said ethoxylated oil comprises an animal oil or a vegetable oil.

5. The transdermal delivery system of claim 1, wherein said ethoxylated oil, comprises an oil selected from the group consisting of castor oil, jojoba oil, corn oil, and emu oil.

6. The transdermal delivery system of claim 1, wherein said delivery agent is a non-steroidal anti inflammatory drug (NSAID).

7. The transdermal delivery system of claim 1, wherein said non-steroidal anti inflammatory drug (NSAID) is selected from the group consisting of ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (–)); phenylbutazone (4-butyl-1,2-diphenyl-3,5-pyrazolidinedione); sulindac-(2)-5-fuoro-2-methyl-1-[[p-(methylsulfinyl)phenyl]methylene-]-1H-indene-3-acetic acid; diflunisal (2',4',-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl) amino]pentyl]ethylamino}ethanol sulfate (1:1); penicillamine (3-mercapto-D-valine); flurbiprofen ([1,1-biphenyl]-4-acetic acid, 2-fluoro-alphamethyl-, (+–.)); cetodolac (1-8-diethyl-13,4,9, tetra hydropyrano-[3-4-13]indole-1-acetic acid; mefenamic acid (N-(2,3-xylyl) anthranilic acid; and diphenhydramine hydrochloride (2-diphenyl methoxy-N, N-di-methylethamine hydrochloride).

8. The transdermal delivery system of claim 1, wherein the delivery agent is a collagen or fragment thereof.

9. The transdermal delivery system of claim 8, wherein the collagen has an approximate average molecular weight from about 2,000 daltons to about 500,000 daltons.

10. The transdermal delivery system of claim 8, wherein the therapeutically effective amount of collagen by weight or volume is 0.1% to 50.0%.

11. The transdermal delivery system of claim 8, wherein the collagen has an approximate average molecular weight of about 2,000 daltons and the therapeutically effective amount by weight or volume is 0.1% to 50.0%.

12. The transdermal delivery system of claim 8, wherein the collagen has an approximate average molecular weight of about 300,000 daltons and the therapeutically effective amount is 0.1% to 2.0%.

13. The transdermal delivery system of claim 8, wherein the collagen has an approximate average molecular weight of about 500,000 daltons and the therapeutically effective amount by weight or volume is 0.1% to 4.0%.

14. A method of reducing pain or inflammation comprising:
   identifying a subject in need of a reduction in pain or inflammation; and
   providing said subject a transdermal delivery system according to claim 1.

15. The method of claim 14, wherein said aqueous adjuvant comprises *Aloe vera*.

16. The method of claim 14, wherein said aqueous adjuvant comprises water.

17. The method of claim 14, wherein said ethoxylated oil comprises an animal oil or a vegetable oil.

18. The method of claim 14, wherein said ethoxylated oil comprises an oil selected from the group consisting of castor oil, jojoba oil, corn oil, and emu oil.

19. The method of claim 14, wherein said delivery agent is a non-steroidal anti inflammatory drug (NSAID).

20. The method of claim 14, wherein said non-steroidal anti inflammatory drug (NSAID) is selected from the group consisting of ibuprofen (2-(isobutylphenyl)-propionic acid); methotrexate (N-[4-(2,4 diamino 6-pteridinyl-methyl] methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (–)); phenylbutazone (4-butyl-1,2-diphenyl-3,5-pyrazolidinedione); sulindac-(2)-5-fuoro-2-methyl-1-[[p-(methylsulfinyl)phenyl]methylene-]-1H-indene-3-acetic acid; diflunisal (2',4',-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl) amino]pentyl] ethylamino}ethanol sulfate (1:1); penicillamine (3-mercapto-D-valine); flurbiprofen ([1,1-biphenyl]-4-acetic acid, 2-fluoro-alphamethyl-, (+–.)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N, N-di-methylethamine hydrochloride).

21. A method of treating or preventing cancer and Alzheimer's disease comprising the step of identifying a subject in need of a COX enzyme inhibitor and administering to said subject a transdermal delivery system according to claim 19 or 20.

22. A method of reducing wrinkles in the skin comprising:
   identifying a subject in need of skin tone restoration; and
   providing to said subject a transdermal delivery system according to claim 1.

23. The method of claim 22, wherein said aqueous adjuvant comprises *Aloe vera*.

24. The method of claim 22, wherein said aqueous adjuvant comprises water.

25. The method of claim 22, wherein said ethoxylated oil comprises an animal oil or a vegetable oil.

26. The method of claim 22, wherein said ethoxylated oil comprises an oil selected from the group consisting of castor oil, jojoba oil, corn oil, and emu oil.

27. The method of claim 22, wherein said delivery agent is a collagen or fragment thereof.

28. The method of claim 22, wherein said collagen has an approximate average molecular weight from about 2,000 daltons to about 500,000 daltons.

29. The method of claim 22, wherein said collagen has an approximate average molecular weight of about 2,000 daltons.

30. The method of claim 22, wherein said collagen has an approximate average molecular weight of about 300,000 daltons and the therapeutically effective amount is 0.1% to 2.0%.

31. The method of claim 22, wherein said collagen has an approximate average molecular weight of about 500,000 daltons and the therapeutically effective amount by weight or volume is 0.1% to 4.0%.

* * * * *

UNITED STATES PATENT AND TRADEMARK OFFICE
CERTIFICATE OF CORRECTION

PATENT NO. : 6,759,056 B2
DATED : July 6, 2004
INVENTOR(S) : Frederick L. Jordan It is certified that error appears in the above-identified patent and that said Letters Patent is hereby corrected as shown below:

Column 25,
Line 1, please delete "claim 1" and insert therefore -- claim 6 --.
Lines 37, 41, 45 and 49, please delete "therapeutically effective".

Column 26,
Line 1, please delete "claim 14" and insert therefore -- claim 19 --.
Lines 60 and 64, please delete "therapeutically effective".

Signed and Sealed this

Fourth Day of October, 2005

JON W. DUDAS
*Director of the United States Patent and Trademark Office*